United States Patent
Kondo

(10) Patent No.: US 8,282,556 B2
(45) Date of Patent: Oct. 9, 2012

(54) ULTRASONIC DIAGNOSTIC APPARATUS AND RECEPTION FOCUSING PROCESSING METHOD

(75) Inventor: Yuji Kondo, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 304 days.

(21) Appl. No.: 12/656,759

(22) Filed: Feb. 16, 2010

(65) Prior Publication Data
US 2010/0210944 A1     Aug. 19, 2010

(30) Foreign Application Priority Data
Feb. 17, 2009   (JP) ................................ 2009-033784

(51) Int. Cl.
*A61B 8/00*     (2006.01)
(52) U.S. Cl. .................... 600/443; 600/407; 600/437
(58) Field of Classification Search .................. 600/407, 600/437, 443, 446
See application file for complete search history.

(56) References Cited

U.S. PATENT DOCUMENTS

| | | | |
|---|---|---|---|
| 4,584,880 A * | 4/1986 | Matzuk | 73/609 |
| 4,835,689 A * | 5/1989 | O'Donnell | 250/580 |
| 5,667,373 A * | 9/1997 | Wright et al. | 600/443 |
| 2004/0223651 A1* | 11/2004 | Ottesen et al. | 382/232 |
| 2006/0256216 A1* | 11/2006 | Takahiko et al. | 348/264 |

FOREIGN PATENT DOCUMENTS

JP     07-303638     11/1995

* cited by examiner

*Primary Examiner* — Tse Chen
*Assistant Examiner* — Joel F Brutus
(74) *Attorney, Agent, or Firm* — Jean C. Edwards, Esq.; Edwards Neils PLLC

(57) ABSTRACT

An ultrasonic diagnostic apparatus realizes reception focusing processing of performing high-accuracy phase-matching and addition on complex baseband signals by using more continuous amounts of delay than those in conventional reception focusing processing. The apparatus includes: a signal processing unit for generating a complex baseband signal based on a reception signal outputted from each of ultrasonic transducers; a first computing unit for obtaining an amplitude value and a phase value of the complex baseband signal; a phase correcting unit for correcting the phase value; a second computing unit for obtaining a real number component or an imaginary number component of the complex baseband signal based on the amplitude value and the corrected phase value; and an adding unit for adding real number components or imaginary number components of complex baseband signals obtained with respect to the ultrasonic transducers to generate a phase-matched and added signal.

7 Claims, 10 Drawing Sheets

FIG.3
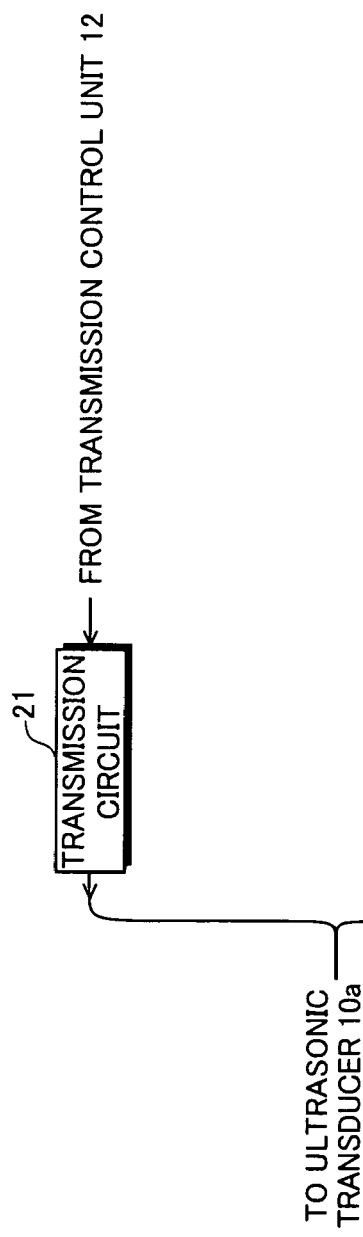
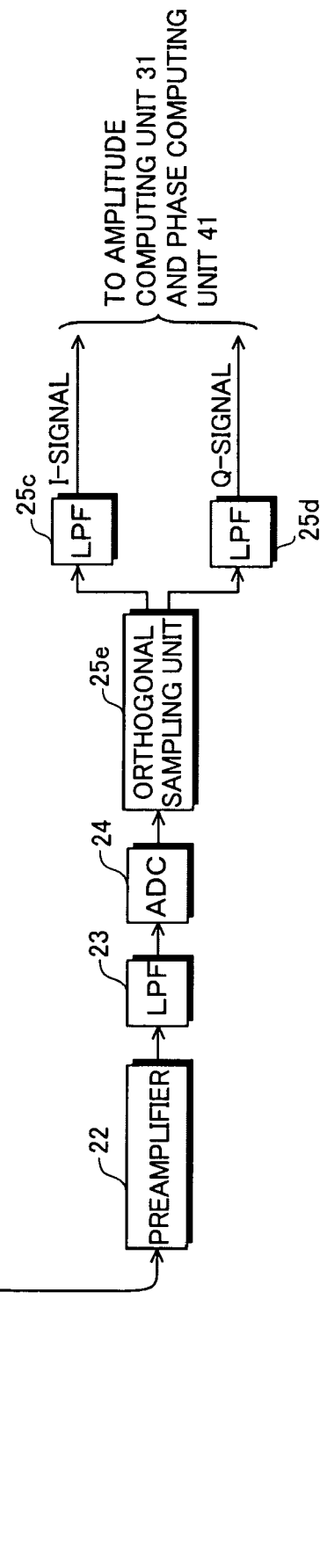

(a)

(b)

FIG.12
PRIOR ART
(a) 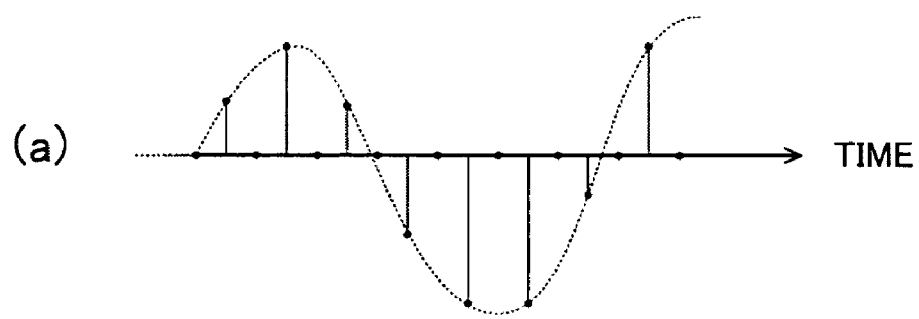 TIME
(b) 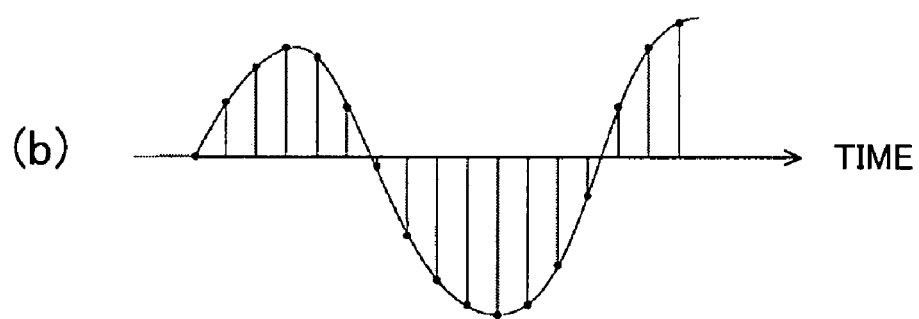 TIME
FIG.13
PRIOR ART
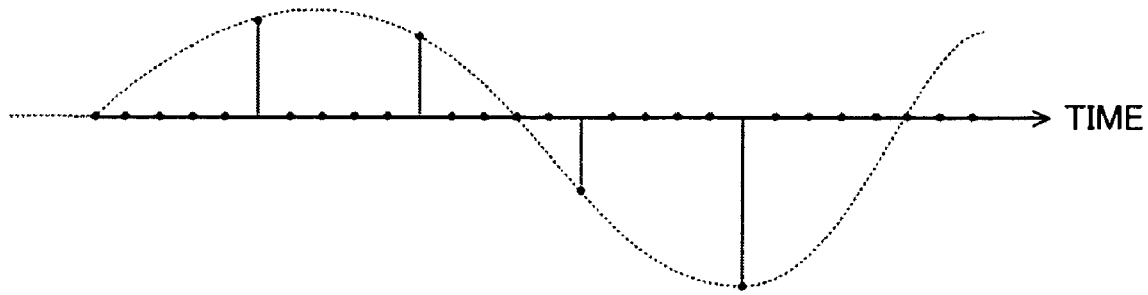 TIME

ULTRASONIC DIAGNOSTIC APPARATUS AND RECEPTION FOCUSING PROCESSING METHOD

CROSS-REFERENCE TO RELATED APPLICATION

The present application claims priority from Japanese Patent Application No. 2009-033784 filed on Feb. 17, 2009, the contents of which are incorporated herein by reference in their entirety.

BACKGROUND OF THE INVENTION

1. Field of the Invention

The present invention relates to an ultrasonic diagnostic apparatus for transmitting and receiving ultrasonic waves to generate an ultrasonic diagnostic image and a reception focusing processing method to be used in the ultrasonic diagnostic apparatus.

2. Description of a Related Art

In medical fields, various imaging technologies have been developed for observation and diagnoses within an object to be inspected. Especially, ultrasonic imaging for acquiring interior information of the object by transmitting and receiving ultrasonic waves enables image observation in real time and provides no exposure to radiation unlike other medical image technologies such as X-ray photography or RI (radio isotope) scintillation camera. Accordingly, ultrasonic imaging is utilized as an imaging technology at a high level of safety in a wide range of departments including not only the fetal diagnosis in obstetrics, but gynecology, circulatory system, digestive system, and so on.

The principle of ultrasonic imaging is as follows. Ultrasonic waves are reflected at a boundary between regions having different acoustic impedances like a boundary between structures within the object. Therefore, by transmitting ultrasonic beams into the object such as a human body and receiving ultrasonic echoes generated within the object, and obtaining reflection points, where the ultrasonic echoes are generated, and reflection intensity, outlines of structures (e.g., internal organs, diseased tissues, and so on) existing within the object can be extracted.

Generally, in an ultrasonic diagnostic apparatus, an ultrasonic probe including plural ultrasonic transducers (vibrators) having transmitting and receiving functions of ultrasonic waves is used. Reception signals outputted from the vibrators that have received ultrasonic echoes have delays according to differences of distances between the focal point of ultrasonic waves and the respective vibrators. Accordingly, by providing delays according to the positions of the vibrators to those reception signals and adding those reception signals to one another, beam forming processing (reception focusing processing) of forming a focal point in a specific position is performed.

In a system of analog beam forming, a delay time can be set according to a pitch of a tap of an analog delay line (delay element) in steps of several tens of nanoseconds. On the other hand, in a system of digital beam forming, basically, a delay time depends on clock fineness in analog/digital conversion. For example, when sampling at 50 MHz is performed, the delay time can be set in steps of 20 ns.

The pitch in the amounts of delay may cause so-called quantization sidelobes, and therefore, efforts are made for a finer pitch. For example, data in locations between adjacent two sampling points are generated by interpolation, or data in locations between adjacent two sampling points are generated by inserting zero values into data (actual data) obtained by reception of ultrasonic echoes, and then performing low-pass filter processing thereon.

As a related technology, Japanese Patent Application Publication JP-A-7-303638 discloses a multi-channel digital receiving apparatus for acquiring in-phase components and orthogonal components from signals respectively reaching plural channels from one signal source through different transfer pathways, by digital processing. The receiving apparatus includes plural channels of receiving means for respectively receiving signals reaching from one signal source through different transfer pathways to output analog reception signals, plural channels of A/D converting means for converting the respective analog reception signals into digital data, a memory for storing the digital data, writing control means for sampling the digital data at a predetermined sampling interval $\Delta T$ to write the digital data in the memory, readout control means for reading out two or more pieces of digital data having sampling times near time $t_m$ shifted from certain target time $t_0$ by a time period $T_m$ of the integral multiple of the sampling interval $\Delta T$, interpolation computing means for computing interpolated digital data at time $t_k$ shifted from time $t_m$ by a time period $\tau_k$ smaller than the sampling interval $\Delta T$ by interpolation computation using the two or more pieces of digital data read out from the memory, sign inverting means for inverting the sign of the interpolated digital data, a switching selecting means for selecting the interpolated digital data, the digital data with the inverted sign, or "0" according to the target time $t_o$, low-pass filter means for extracting only basebands and outputting the basebands as channel in-phase components or channel orthogonal components, in-phase component adding means for adding in-phase components of the respective channels to acquire a synthesized in-phase component, and orthogonal component adding means for adding orthogonal components of the respective channels to acquire a synthesized orthogonal component.

FIG. 8 is a waveform chart for explanation of sampling and data delay in conventional beam forming. According to the conventional method, ultrasonic reception signals are phase-matched and added to one another in a form of RF signals. In digital beam forming, delaying of data is performed by adjusting the readout timings of data stored in a memory. However, the data stored in the memory exist at a time interval of a sampling period, and are coarse for setting amounts of delay. Generally, when coarse amounts of delay are set, so-called quantization sidelobes are generated, and image quality becomes deteriorated because the obtained image contains artifacts.

Accordingly, as shown in FIG. 9, it is required to set a finer amount of delay than the sampling period. Here, FIG. 9(a) shows original data, and FIG. 9(b) shows data delayed by a time period "t". As a method of interpolating data between actual data, there are methods of linearly interpolating data between adjacent two pieces of actual data as shown in FIG. 10, interpolating data by using a spline function as shown in FIG. 11, and so on. Further, because of the simple circuit configuration, as shown in FIG. 12, a method of generating interpolated data by inserting zero data between actual data and performing low-pass filter processing thereon. Here, FIG. 12(a) shows a state in which the zero data has been inserted, and FIG. 12(b) shows a state in which the low-pass filter processing has been performed.

On the other hand, it is also possible that the reception signals (RF signals) are orthogonally detected and complex baseband signals (I-signals and Q-signals) are generated, and then, the complex baseband signals are provided with delays for phase-matching and added to one another. For just performing orthogonal detection, conditions are the same as those of phase-matching and addition of the above-mentioned RF signals. After the orthogonal detection, the signal band is narrow, and resampling can be performed at a sampling frequency equal to or more than twice the signal band. That is, by resampling at a slow sampling clock of about a fraction of the sampling clock of the original RF signals, the number of data can be reduced.

However, at the same time, the sampling period of data becomes coarser. Accordingly, in the case of generating the finer amount of delay by the above-mentioned interpolation processing, several times of data interpolation processing of the RF signals is required as shown in FIG. 13.

SUMMARY OF THE INVENTION

The present invention has been achieved in view of the above-mentioned problems. A purpose of the present invention is to realize reception focusing processing of performing high-accuracy phase-matching and addition on complex baseband signals obtained by orthogonal detection or the like by using more continuous amounts of delay than those in conventional reception focusing processing without performing data interpolation processing.

In order to accomplish the above-mentioned purpose, an ultrasonic diagnostic apparatus according to one aspect of the present invention includes: a plurality of ultrasonic transducers for transmitting ultrasonic waves according to drive signals and receiving ultrasonic echoes to output reception signals; signal processing means for performing one of orthogonal detection processing and orthogonal sampling processing on a reception signal outputted from each of the plurality of ultrasonic transducers to generate a complex baseband signal; first computing means for obtaining an amplitude value and a phase value of the complex baseband signal generated by the signal processing means; phase correcting means for correcting the phase value obtained by the first computing means according to relative positions of a reception focus and the plurality of ultrasonic transducers; second computing means for obtaining a real number component and/or an imaginary number component of the complex baseband signal based on the amplitude value obtained by the first computing means and the phase value corrected by the phase correcting means; and adding means for adding real number components of complex baseband signals obtained with respect to the plurality of ultrasonic transducers by the second computing means to one another to generate a phase-matched and added real number signal, and/or adding imaginary number components of the complex baseband signals obtained with respect to the plurality of ultrasonic transducers by the second computing means to one another to generate a phase-matched and added imaginary number signal.

Further, a reception focusing processing method according to one aspect of the present invention includes the steps of: (a) generating a complex baseband signal by performing one of orthogonal detection processing and orthogonal sampling processing on a reception signal outputted from each of plurality of ultrasonic transducers for transmitting ultrasonic waves according to drive signals and receiving ultrasonic echoes to output reception signals; (b) obtaining an amplitude value and a phase value of the complex baseband signal generated at step (a); (c) correcting the phase value obtained at step (b) according to relative positions of a reception focus and the plurality of ultrasonic transducers; (d) obtaining a real number component and/or an imaginary number component of the complex baseband signal based on the amplitude value obtained at step (b) and the phase value corrected at step (c); and (e) adding real number components of complex baseband signals obtained with respect to the plurality of ultrasonic transducers at step (d) to one another to generate a phase-matched and added real number signal, and/or adding imaginary number components of the complex baseband signals obtained with respect to the plurality of ultrasonic transducers at step (d) to one another to generate a phase-matched and added imaginary number signal.

According to the one aspect of the present invention, the orthogonal detection processing or the orthogonal sampling processing is performed on the reception signal to generate the complex baseband signal and the amplitude value and the phase value thereof are obtained, the real number component or the imaginary number component of the complex baseband signal is obtained by correcting the phase value according to the relative positions of the reception focus and the plurality of ultrasonic transducers, and the real number components or the imaginary number components of the complex baseband signals obtained with respect to the plurality of ultrasonic transducers are added to one another, and thereby, reception focusing processing of performing high-accuracy phase-matching and addition on the complex baseband signals obtained by orthogonal detection or the like by using more continuous amounts of delay than those in conventional reception focusing processing can be realized without performing data interpolation processing.

BRIEF DESCRIPTION OF THE DRAWINGS

FIG. 3 shows a second configuration example of a transmitting and receiving unit as shown in FIG. 1;

FIG. 12 is a waveform chart for explanation of data interpolation using low-pass filter processing; and FIG. 13 is a waveform chart for explanation of data interpolation on a complex baseband signal.

DESCRIPTION OF THE PREFERRED EMBODIMENTS

Figure 1:
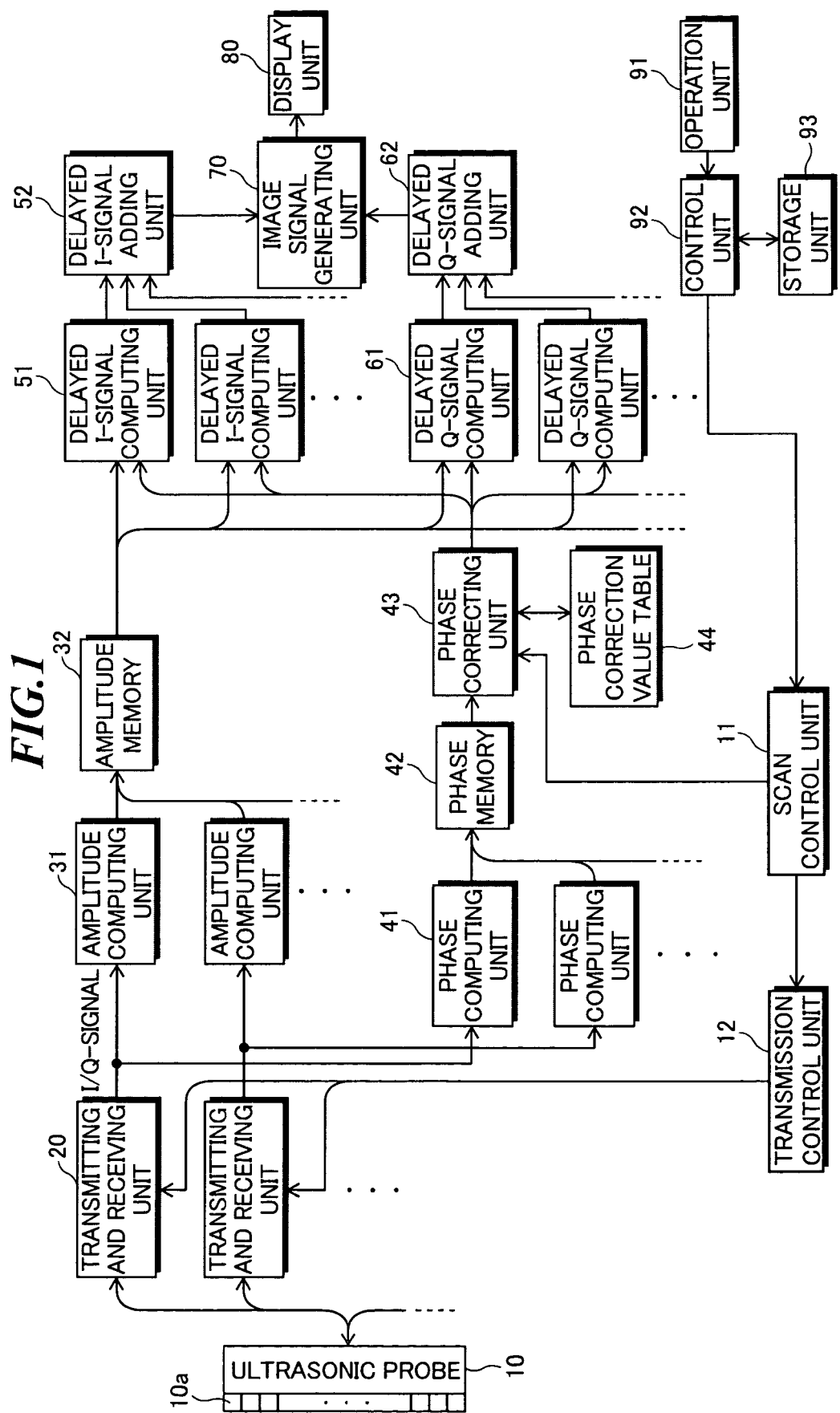
FIG. 1 is a block diagram showing a configuration of an ultrasonic diagnostic apparatus according to one embodiment of the present invention.

Hereinafter, embodiments of the present invention will be explained in detail with reference to the drawings. The same reference characters are assigned to the same component elements and the explanation thereof will be omitted.

FIG. 1 is a block diagram showing a configuration of an ultrasonic diagnostic apparatus according to one embodiment of the present invention. The ultrasonic diagnostic apparatus includes an ultrasonic probe 10, a scan control unit 11, a transmission control unit 12, transmitting and receiving units 20, amplitude computing units 31, an amplitude memory 32, phase computing units 41, a phase memory 42, a phase correcting unit 43, a phase, correction value table 44, delayed I-signal computing units 51, a delayed I-signal adding unit 52, delayed Q-signal computing units 61, a delayed Q-signal adding unit 62, an image signal generating unit 70, an operation unit 91, a control unit 92, and a storage unit 93.

The ultrasonic probe 10 includes plural ultrasonic transducers 10a forming a one-dimensional or two-dimensional transducer array, and may be an external probe of linear-scan type, convex-scan type, sector-scan type, or the like, or an ultrasonic endoscopic probe of radial-scan type or the like.

The plural ultrasonic transducers 10a transmit ultrasonic waves according to applied drive signals, and receive propagating ultrasonic echoes to output reception signals. Each ultrasonic transducer includes a vibrator having electrodes formed on both ends of a material having a piezoelectric property (piezoelectric material) such as a piezoelectric ceramic represented by PZT (Pb (lead) zirconate titanate), a polymeric piezoelectric element represented by PVDF (polyvinylidene difluoride), or the like.

When a pulsed or continuous wave voltage is applied to the electrodes of the vibrator, the piezoelectric material expands and contracts. By the expansion and contraction, pulse or continuous wave ultrasonic waves are generated from the respective vibrators, and an ultrasonic beam is formed by synthesizing these ultrasonic waves. Further, the respective vibrators expand and contract by receiving the propagating ultrasonic waves to generate electric signals. These electric signals are outputted as reception signals of ultrasonic waves.

The scan control unit 11 sequentially set transmission directions of an ultrasonic beam and reception directions of ultrasonic echoes. The transmission control unit 12 selects one transmission delay pattern from among plural transmission delay patterns according to the transmission direction set by the scan control unit 11, and sets delay times to be provided to the drive signals for the plural ultrasonic transducers 10a based on the selected transmission delay pattern. Alternatively, the transmission control unit 12 may set delay times such that the ultrasonic waves transmitted at a time from the plural ultrasonic transducers 10a reach the entire imaging region of the object.

The plural channels of transmitting and receiving units 20 generate drive signals under the control of the transmission control unit 12 and supply those drive signals to the plural ultrasonic transducers 10a. Further, the transmitting and receiving units 20 perform orthogonal detection processing or orthogonal sampling processing on reception signals outputted from the ultrasonic transducers 10a to generate complex baseband signals (I-signals and Q-signals), and supply the generated complex baseband signals to the amplitude computing units 31 and the phase computing units 41.

Figure 2:
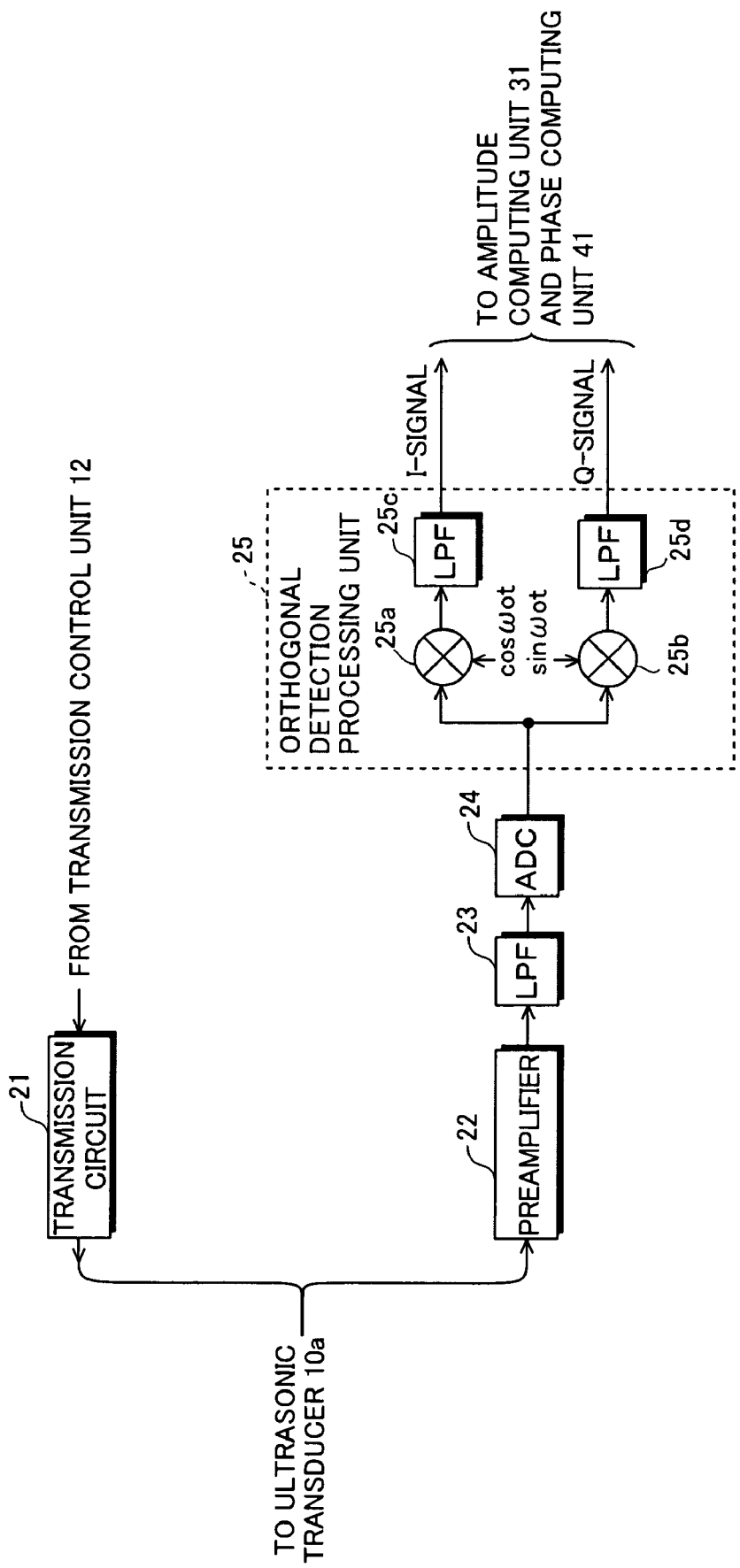
FIG. 2 shows a first configuration example of a transmitting and receiving unit as shown in FIG. 1.

FIG. 2 shows a first configuration example of the transmitting and receiving unit as shown in FIG. 1. As shown in FIG. 2, each channel of transmitting and receiving unit 20 includes a transmission circuit 21, a preamplifier 22, a low-pass filter (LPF) 23, an analog/digital converter (ADC) 24, and an orthogonal detection processing unit 25. Here, the preamplifier 22 to the orthogonal detection processing unit 25 form signal processing means for performing orthogonal detection processing on the reception signal outputted from the corresponding ultrasonic transducer 10a to generate the complex baseband signal.

The transmission circuit 21 includes a pulser, for example, and generates a drive signal under the control of the transmission control unit 12 and supplies the generated drive signal to the ultrasonic transducer 10a. Plural channels of transmission circuits 21 adjust amounts of delay of the drive signals according to the transmission delay pattern selected by the transmission control unit 12 and supply the drive signals to the ultrasonic probe 10 such that the ultrasonic waves transmitted from the plural ultrasonic transducers 10a form an ultrasonic beam, or such that the ultrasonic waves transmitted at a time from the plural ultrasonic transducers 10a reach the entire imaging region of the object.

The preamplifier 22 amplifies the reception signal (RF signal) outputted from the ultrasonic transducer 10a, and the LPF 23 limits a frequency band of the reception signal outputted from the preamplifier 21 to prevent aliasing in A/D conversion. The ADC 24 converts the analog reception signal outputted from the LPF 23 into a digital reception signal.

The orthogonal detection processing unit 25 performs orthogonal detection processing on the reception signal and generates a complex baseband signal (I-signal and Q-signal). As shown in FIG. 2, the orthogonal detection processing unit 25 includes mixers (multiplication circuits) 25a and 25b, and low-pass filters (LPFs) 25c and 25d.

The mixer 25a multiplies the reception signal, which has been converted into the digital signal by the ADC 24, by a local oscillation signal $\cos \omega_0 t$, and the LPF 25c performs low-pass filter processing on the signal outputted from the mixer 25a, and thereby, an I-signal representing a real number component of the complex baseband signal is generated. On the other hand, the mixer 25b multiplies the reception signal, which has been converted into the digital signal by the ADC 24, by a local oscillation signal $\sin \omega_0 t$, which is obtained by shifting the phase of the local oscillation signal $\cos \omega_0 t$ by $\pi/2$, and the LPF 25d performs low-pass filter processing on the signal outputted from the mixer 25b, and thereby, a Q-signal representing an imaginary number component of the complex baseband signal is generated. The generated complex baseband signal is supplied to the amplitude computing unit 31 and the phase computing unit 41 as shown in FIG. 1.

FIG. 3 shows a second configuration example of the transmitting and receiving unit as shown in FIG. 1. In the second configuration example as shown in FIG. 3, an orthogonal sampling unit 25e is provided in place of the mixers 25a and 25b in the first configuration example as shown in FIG. 2. The rest of the configuration is the same as that in the first configuration example.

Figure 4:
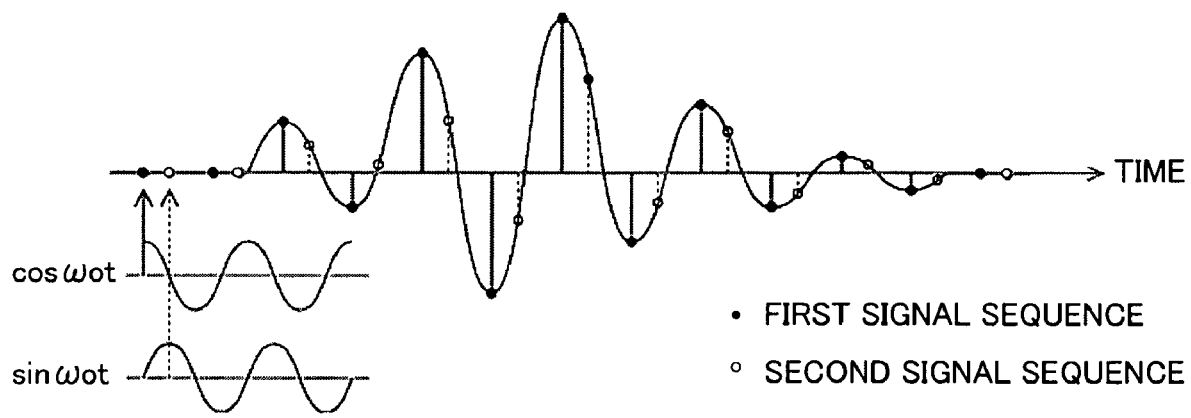
FIG. 4 is a waveform chart for explanation of an operation of an orthogonal sampling unit as shown in FIG. 3.

FIG. 4 is a waveform chart for explanation of an operation of the orthogonal sampling unit as shown in FIG. 3. The orthogonal sampling unit 25e generates a first signal sequence by sampling the reception signal, which has been converted into the digital signal by the ADC 24, in synchronization with the phase of $\cos \omega_0 t$, and generates a second signal sequence by sampling the reception signal in synchronization with the phase of $\sin \omega_0 t$.

Referring to FIG. 3 again, the LPF 25c performs low-pass filter processing on the first signal sequence outputted from the orthogonal sampling unit 25e to generate an I-signal representing a real number component of the complex baseband signal, and the LPF 25d performs low-pass filter processing on the second signal sequence outputted from the orthogonal sampling unit 25e to generate a Q-signal representing an imaginary number component of the complex baseband signal. Thereby, the mixers 25a and 25b shown in FIG. 2 may be omitted.

In the above-mentioned configuration, the orthogonal detection processing unit 25 (FIG. 2), the orthogonal sampling unit 25e (FIG. 3), and the LPFs 25c and 25d (FIG. 3) may be formed of digital circuits, or formed of a central processing unit (CPU) and software (program) for allowing the CPU to perform various kinds of processing. Alternatively, the orthogonal detection processing unit 25 may be formed of an analog circuit, and the ADC 24 may be omitted. In this case, the A/D conversion is performed by the amplitude computing unit 31 and the phase computing unit 41 as shown in FIG. 1.

Figure 5:
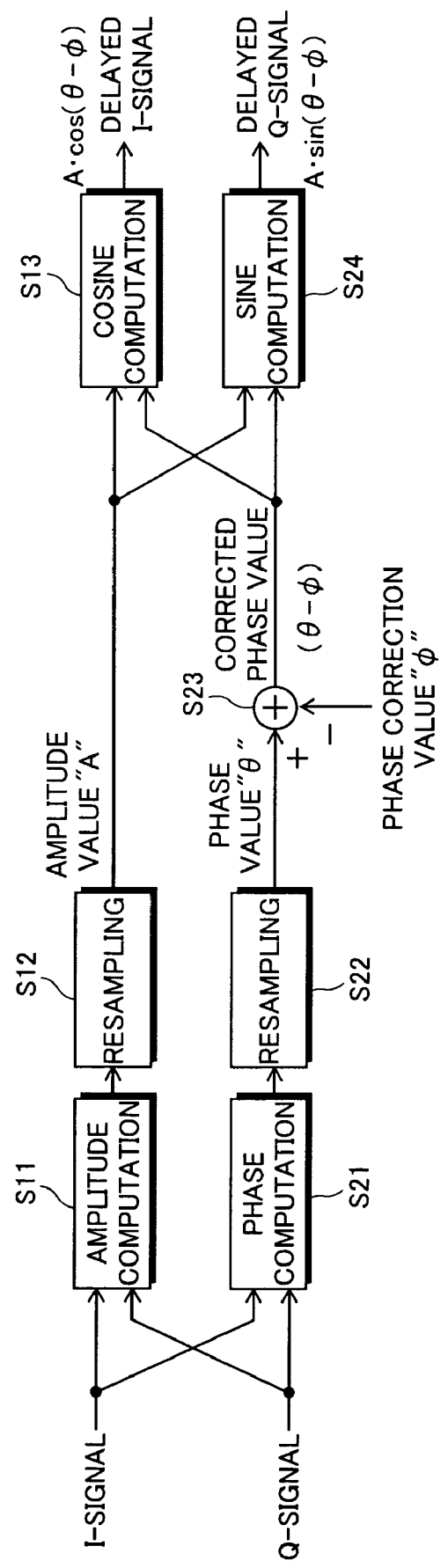
FIG. 5 is a diagram for explanation of operations from amplitude computing units and phase computing units to a delayed I-signal computing units and delayed Q-signal computing units as shown in FIG. 1.

FIG. 5 is a diagram for explanation of operations from amplitude computing units and phase computing units to a delayed I-signal computing units and delayed Q-signal computing units as shown in FIG. 1. FIG. 5 shows signal processing for one channel corresponding to one ultrasonic transducer 10a.

The amplitude computing unit 31 obtains, at step S11, an amplitude value "A" of the complex baseband signal based on the complex baseband signal (I-signal and Q-signal) supplied from the transmitting and receiving unit 20, and resamples the amplitude value "A" of the complex baseband signal at step S12. The amplitude value "A" of the complex baseband signal is stored in the amplitude memory 32.

Further, the phase computing unit 41 obtains, at step S21, a phase value "θ" of the complex baseband signal based on the complex baseband signal (I-signal and Q-signal) supplied from the transmitting and receiving unit 20, and resamples the phase value "θ" of the complex baseband signal at step S12. The phase value "θ" of the complex baseband signal is stored in the phase memory 42. In the case where the sampling rate of the complex baseband signal is used without change, steps S12 and S22 may be omitted.

The phase correction value table 44 stores phase correction values "φ" to be used for correcting the phase value "θ" obtained by the phase computing unit 41, according to the geometric relative positions of the reception focus and the plural ultrasonic transducers 10a. At step S23, the phase correcting unit 43 reads out the phase correction value "φ" from the phase correction value table 44 according to the reception direction set by the scan control unit 11, and subtracts the phase correction value "φ" from the phase value "θ" read out from the phase memory 42, and thereby, obtains a corrected phase value (θ−φ). This corresponds to delaying the complex baseband signal by the time corresponding to the phase correction value "φ".

At step S13, the delayed I-signal computing unit 51 obtains A·cos(θ−φ) as the real number component (delayed I-signal) of the delayed complex baseband signal based on the amplitude value "A" obtained by the amplitude computing unit 31 and the phase value (θ−φ) corrected by the phase correcting unit 43. Further, at step S24, the delayed Q-signal computing unit 61 obtains A·sin(θ−φ) as the imaginary number component (delayed Q-signal) of the delayed complex baseband signal based on the amplitude value "A" obtained by the amplitude computing unit 31 and the phase value (θ−φ) corrected by the phase correcting unit 43.

Referring to FIG. 1 again, the delayed I-signal adding unit 52 performs reception focusing processing by adding the delayed I-signals obtained with respect to the plural ultrasonic transducers 10a by the delayed I-signal computing units 51 to one another. By the reception focusing processing, a phase-matched and added I-signal with the narrowed focus of ultrasonic echoes is generated. Further, the delayed Q-signal adding unit 62 performs reception focusing processing by adding the delayed Q-signals obtained with respect to the plural ultrasonic transducers 10a by the delayed Q-signal computing units 61 to one another. By the reception focusing processing, a phase-matched and added Q-signal with the narrowed focus of ultrasonic echoes is generated.

In this way, by correcting the phase value "θ", reception focusing processing of performing high-accuracy phase-matching and addition on the complex baseband signals obtained by orthogonal detection or the like, by using more continuous amounts of delay than those in the conventional reception focusing processing can be realized without performing data interpolation processing. Further, the phase-matching and adding circuit can be simplified, and the focus can be set at the higher degree of freedom.

The image signal generating unit 70 generates an image signal representing an ultrasonic diagnostic image based on the phase-matched and added I-signal generated by the delayed I-signal adding unit 52 and the phase-matched and added Q-signal generated by the delayed Q-signal adding unit 62. For example, the image signal generating unit 70 generates an image signal representing an ultrasonic diagnostic image based on a square root of a sum of squares of the phase-matched and added I-signal and the phase-matched and added Q-signal (hereinafter, also referred to as "phase-matched and added signal"). In addition, the image signal generating unit 70 can generate an image signal based on one of the phase-matched and added I-signal and the phase-matched and added Q-signal, and in this case, the delayed Q-signal computing units 61 and the delayed Q-signal adding unit 62 may be omitted, or the delayed I-signal computing units 51 and the delayed I-signal adding unit 52 may be omitted.

Here, a principle of the present invention will be explained in detail by referring to FIGS. 6 and 7.

Figure 6:
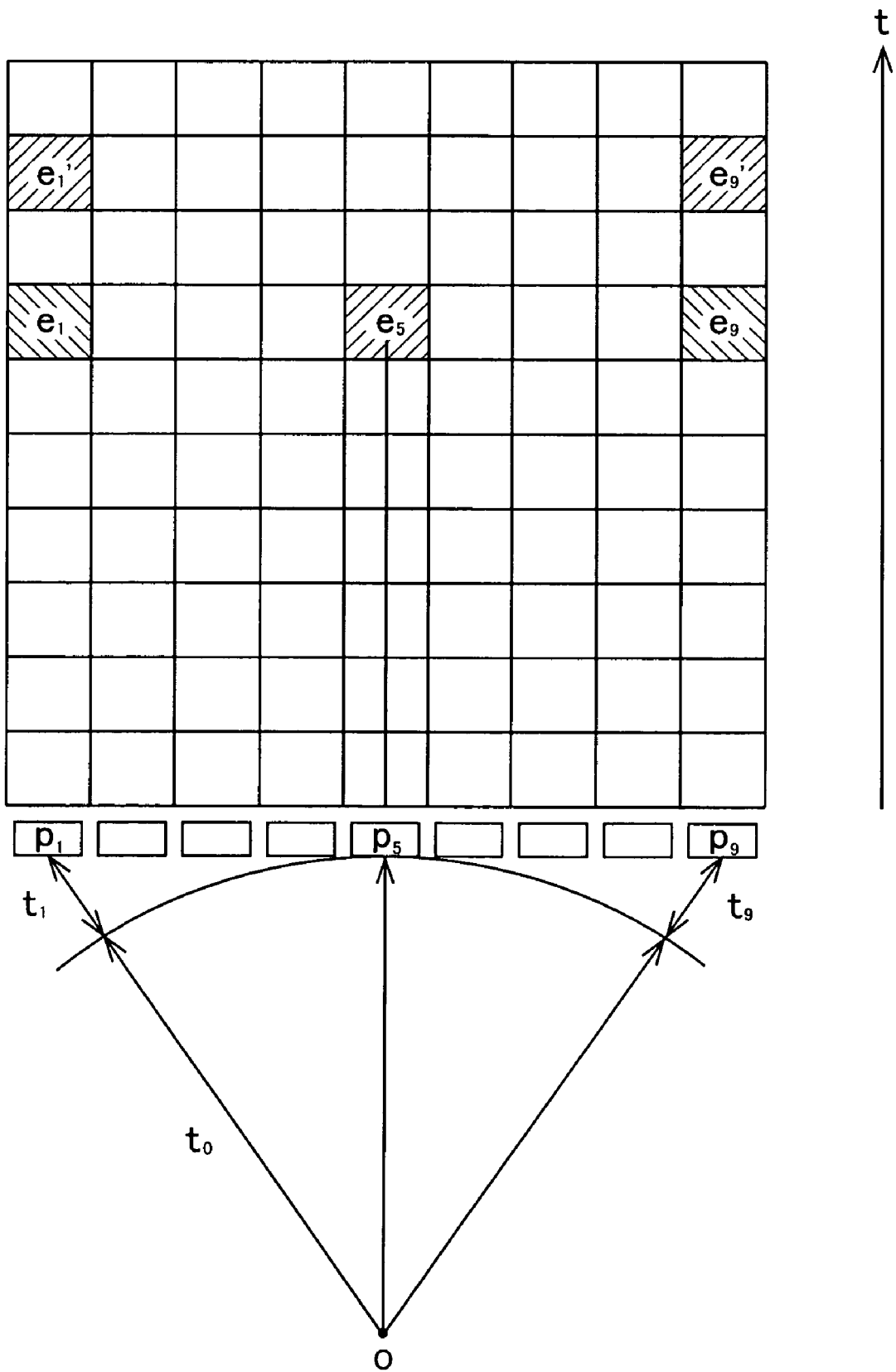
FIG. 6 shows positions of reception signals when arranged vibrators receive ultrasonic echoes reflected from point "O"
Figure 7:
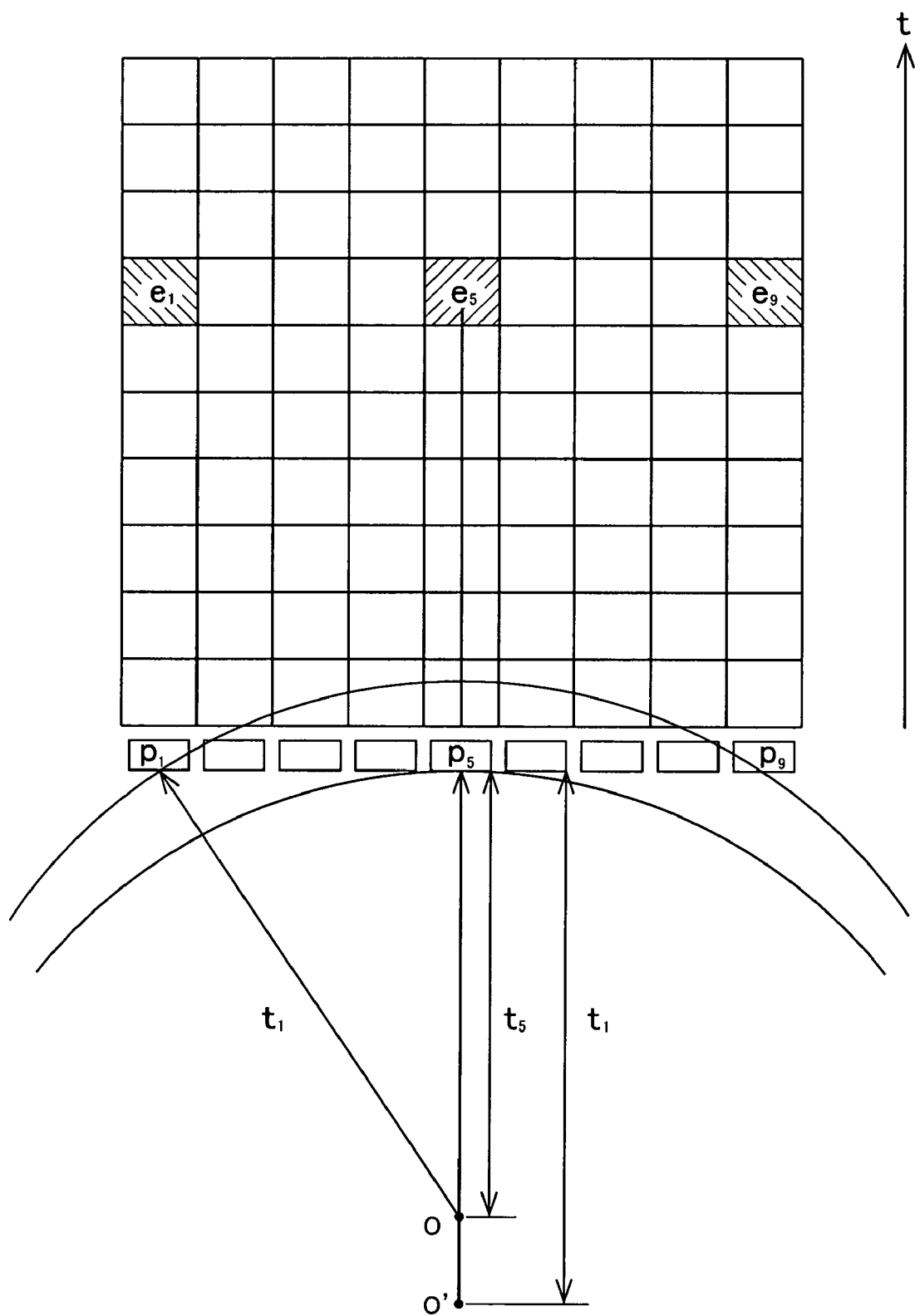
FIG. 7 shows a location of the ultrasonic reflection source with respect to the positions of the reception signals obtained by the arranged vibrators.
Figure 8:
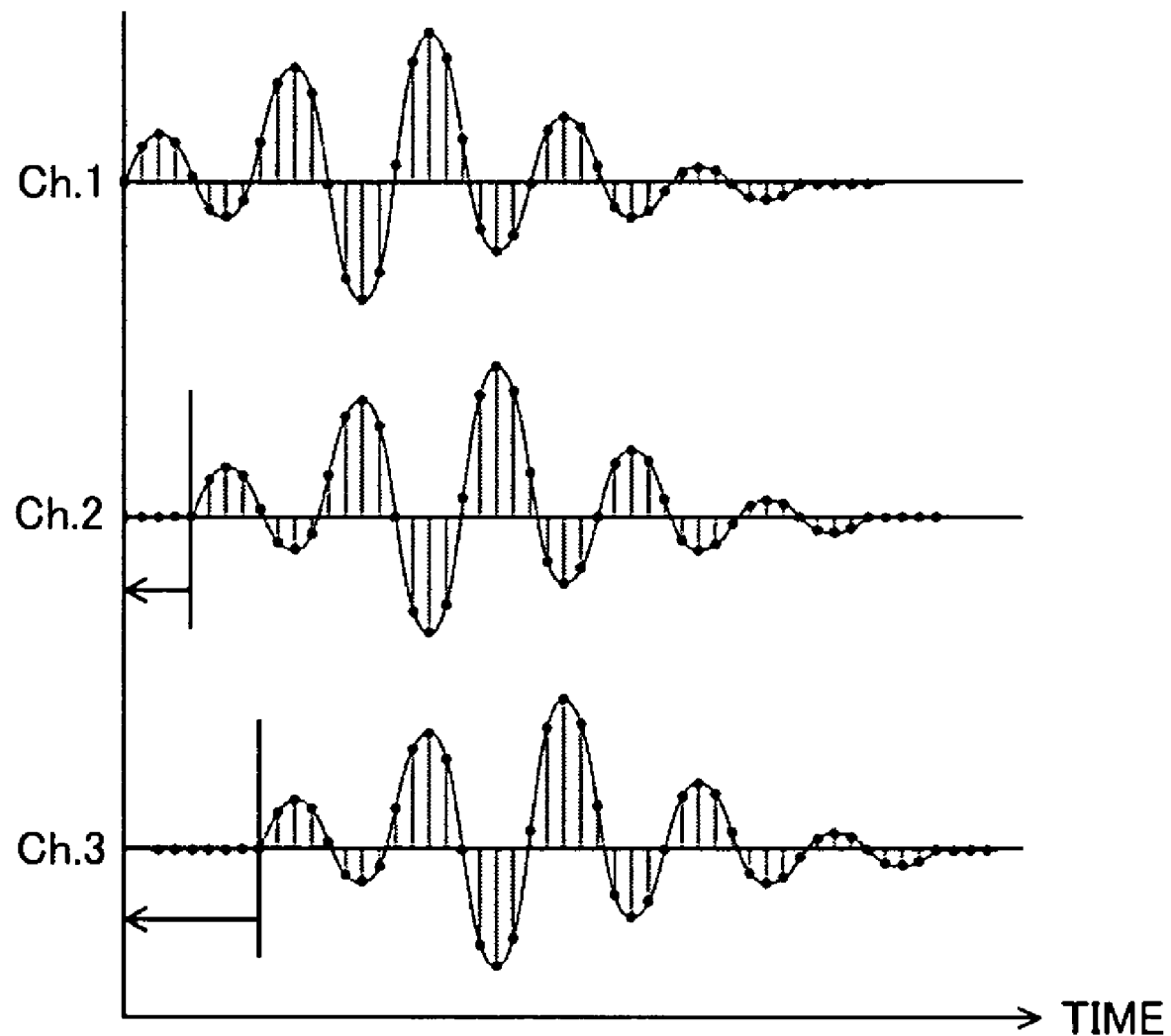
FIG. 8 is a waveform chart for explanation of sampling and data delay in conventional beam forming.
Figure 9:
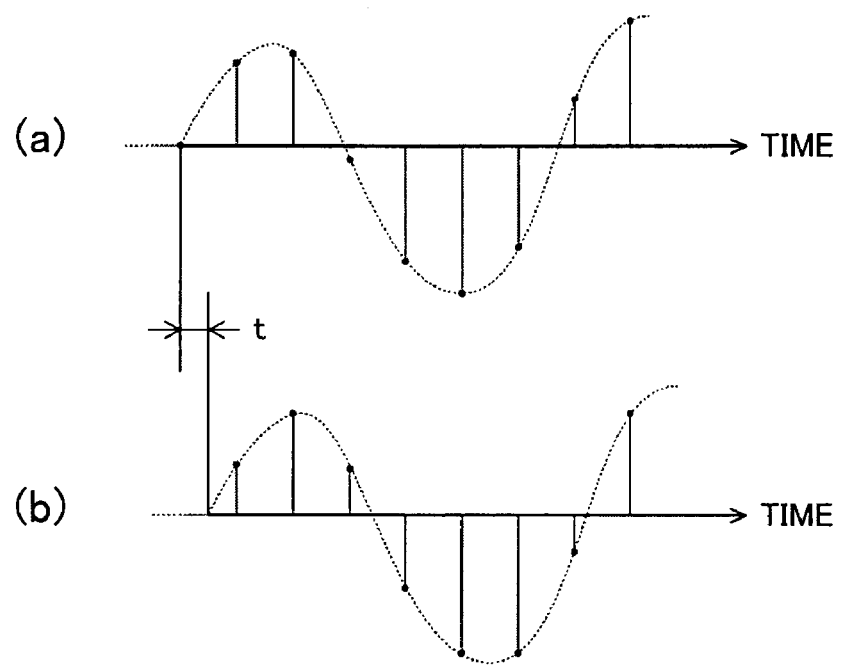
FIG. 9 is a waveform chart for explanation of finer data delay than a sampling period.
Figure 10:
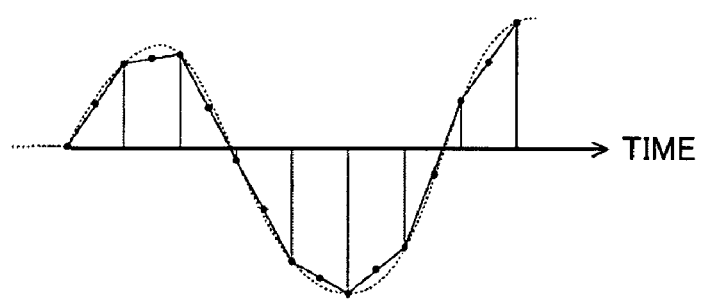
FIG. 10 is a waveform chart for explanation of linear data interpolation.
Figure 11:
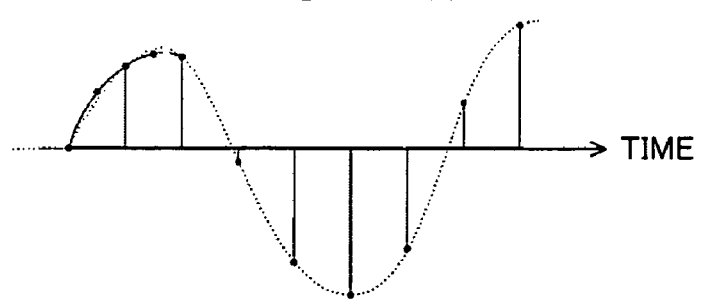
FIG. 11 is a waveform chart for explanation of data interpolation using a spline function.

FIG. 6 shows positions of reception signals when arranged vibrators receive ultrasonic echoes reflected from point "O", and FIG. 7 shows a location of the ultrasonic reflection source with respect to the positions of the reception signals obtained by the arranged vibrators. In FIG. 6, a matrix as shown above vibrators $p_1$-$p_9$ represents digitized reception signals. The columns as shown above the respective vibrators indicate reception signals from the vibrators at time "t". For example, when the vibrator $p_5$ at the center receives ultrasonic echoes from the point "O" at a certain time, the reception signal is stored in a location $e_5$. The reception signals from the vibrators $p_1$ and $p_9$ at ends receiving ultrasonic echoes at the same time are stored in locations $e_1$ and $e_9$.

However, those reception signals represent ultrasonic echoes from distances nearer than the point "O", and the ultrasonic echoes from the point "O" reach with delay times of $t_1$ and $t_9$, respectively. In FIG. 6, the reception signals are stored in locations $e_1'$ and $e_9'$, respectively. If the point "O" is immediately below the vibrator $p_5$, the relation $t_1=t_9$ holds, and the timing of locations $e_1'$ and $e_9'$ are the same. Conventional beam forming employs a method of actually delaying the reception signal in the location $e_5$ by time $t_1$ and adding it to the reception signals in the locations $e_1'$ and $e_9'$.

In FIG. 7, the reception signal e(nT) in the location $e_1$ by the vibrator $p_1$ is assumed to be expressed by the equation (1).

$$e(nT)=A(nT)\cdot\exp\{j(2\pi f_0 nT+\theta_0)\} \qquad (1)$$

where A(nT) is signal intensity of ultrasonic echoes from the point "O", nT represents n-th data AD-converted at a sampling rate with a sampling interval of "T". The reception signal has phase rotation corresponding to the time nT for transmission frequency $f_0$, and $\theta_0$ is an initial value of the phase according to depth. Here, the reception signal $e_i(nT)$ received by another vibrator at the same time is expressed by the equation (2).

$$e_i(nT) = A(nT+t(i,n)) \cdot \exp\{j(2\pi f_0(nT+t(i,n))+\theta_0)\} \quad (2)$$

The reception signal $e_i(nT)$ is a signal from the depth corresponding to the time $t_1$, and therefore, it is a reception signal from point "O'" deeper than the point "O". For example, in FIG. 7, in consideration of the reception signal by the vibrator $p_5$, it precedes by the time $(t_1-t_5)$ compared to the reception signal in the location $e_1$. The time difference is obtained by the location of the vibrator and the reception time, and the time difference can be expressed as $t(i, n)$. Further, $t(i, n)$ can be calculated from the geometric relative positions of the sound source and the vibrator. In the conventional beam forming, the reception signal $e_i(nT)$ is delayed by the time difference $t(i, n)$ such that the reception signal $e_i(nT)$ is in phase with the reception signal $e(nT)$, and those reception signals are added to one another, and thus, phase-matching and addition is performed.

In the baseband method, the reception signal is orthogonally detected or orthogonally sampled, and thereby, the reception signal is converted into an I-signal and a Q-signal in the baseband. The reception signals expressed by the equations (1) and (2) are converted into the baseband and expressed by the equations (3) and (4).

$$E(nT) = e(nT) \cdot \exp\{-j(2\pi f_0 nT)\} \quad (3)$$
$$= A(nT) \cdot \exp\{-j\theta_0\}$$

$$E_i(nT) = e_i(nT) \cdot \exp\{-j(2\pi f_0 nT)\} \quad (4)$$
$$= A(nT+t(i,n)) \cdot \exp\{j(2\pi f_0 t(i,n)+\theta_0)\}$$

Here, when $t(i, n) > nT$, the sample point "n" may be changed to obtain the condition of $t(i, n) < nT$. For example, the replacement of $t(i, n) = mT+t_i$ is possible, and m-th data is used in place of the n-th data in $E_i(nT)$. That means using data corresponding to different depths in the memory, where the relation $t_i < T$ holds. If the time is before re-sampling, the relation $T < 1/(2f_0)$ holds, and therefore, the relation $2\alpha f_0 t_i < \pi$ holds. This shows that the delay of "T" or more can be corrected by using the data at a different sample point, and correction of the data at the same sample point may be performed only on the delay $t_i$ less than "T". From that, the equation (4) can be replaced by the equation (5).

$$E_i(nT) = A(mT+t_i) \cdot \exp\{j(2\pi f_0 t_i + \theta_0)\} \quad (5)$$

Here, in consideration that $t_i$ is sufficiently small, $A(mT+t_i)$ is thought to be smaller than the resolving power and can be replaced by $A(nT)$. For simplification, replacement is performed as expressed by the equations (6) and (7). Here, An and $\theta n_i$ are an amplitude and a phase after orthogonal detection, respectively.

$$A(mT+t_i) = A(nT) = An \quad (6)$$

$$2\pi f_0 t_i + \theta_0 = \theta n_i \quad (7)$$

Accordingly, delaying the signal in the equation (5) by the time $t_i$ corresponds to turning back the phase by the amount corresponding to the time $t_i$. Therefore, the I-signal and the Q-signal can be obtained by the equations (8) and (9), respectively.

$$Rn_{i=An} \cdot \cos\{\theta n_i - \phi(i, n)\} \quad (8)$$

$$In_{i=An} \cdot \sin\{\theta n_i - \phi(i, n)\} \quad (9)$$

Here, $\phi(i, n)$ is expressed by the equation (10) and can be calculated from the geometric relative positions of the sound source and the vibrator.

$$\phi(i, n) = 2\pi f_0 t(i, n) \quad (10)$$

The I-signals obtained by the equation (8) in the number of vibrators are added to one another, and thereby, a phase-matched and added I-signal Rn can be obtained as expressed by the equation (11). Similarly, the Q-signals obtained by the equation (9) in the number of vibrators are added to one another, and thereby, a phase-matched and added Q-signal In can be obtained as expressed by the equation (12).

$$Rn = \sum_i Rn_i \quad (11)$$

$$In = \sum_i In_i \quad (12)$$

For image display, a phase-matched and added signal Vn may be calculated as expressed by the equation (13) based on the signals Rn and In in equations (11) and (12), for example.

$$Vn = \sqrt{Rn^2 + In^2} \quad (13)$$

The image signal generating unit 70 as shown in FIG. 1 includes an STC (sensitivity time control) part, and a DSC (digital scan converter). The STC part performs attenuation correction by distance according to the depths of the reflection positions of ultrasonic waves on the phase-matched and added signal. The DSC converts (raster-converts) the phase-matched and added signal corrected by the STC part into an image signal that follows the normal scan system of television signals and performs necessary image processing such as gradation processing to generate a B-mode image signal. Here, the B-mode refers to a mode of displaying a two-dimensional tomographic image by converting the amplitudes of ultrasonic echoes into brightness. The display unit 80 includes a display device such as an LCD, and displays an ultrasonic diagnostic image based on the B-mode image signal generated by the image signal generating unit 70.

The control unit 92 controls the scan control unit 11 and so on according to the operation of an operator using the operation unit 91. In the embodiment, the scan control unit 11, the transmission control unit 12, the amplitude computing unit 31, the phase computing unit 41, the phase correcting unit 43, the delayed I-signal computing units 51, the delayed I-signal adding unit 52, the delayed Q-signal computing units 61, the delayed Q-signal adding unit 62, the image signal generating unit 70, and the control unit 92 are formed of a CPU and software (program) for allowing the CPU to perform various kinds of processing, but they may be formed of digital circuits or analog circuits. The software (program) is stored in the storage unit 93. As a recording medium in the storage unit 93, not only a built-in hard disk but also a flexible disk, MO, MT, RAM, CD-ROM, DVD-ROM, or the like may be used.

The invention claimed is:
1. An ultrasonic diagnostic apparatus comprising:
    a plurality of ultrasonic transducers for transmitting ultrasonic waves according to drive signals and receiving ultrasonic echoes to output reception signals;
    signal processing units each performing one of quadrature detection processing and quadrature sampling processing on a reception signal outputted from respective one of said plurality of ultrasonic transducers to generate a complex baseband signal;

first computing units each obtaining an amplitude value signal representing an amplitude value of the complex baseband signal and a phase value signal representing a phase value of the complex baseband signal generated respective one of by said signal processing means units, the amplitude value signal and the phase value signal having a predetermined sampling interval;

a phase correction value table for storing phase correction values to be used for correcting the phase value for a time difference according to relative positions of a reception focus and said plurality of ultrasonic transducers, the phase correction values including at least one phase correction value to be used for correcting the phase value for the time difference finer than the predetermined sampling interval;

a phase correcting unit for reading out a phase correction value from said phase correction value table according to a reception direction and correcting the phase value obtained by each of said first computing units by using the phase correction value;

second computing units each obtaining a real number component and an imaginary number component of a corrected complex baseband signal represented by the amplitude value obtained by respective one of said first computing units and the phase value corrected by said phase correcting unit; and an adding unit for adding real number components of corrected complex baseband signals obtained with respect to said plurality of ultrasonic transducers by said second computing units to one another to generate a phase-matched and added real number signal, and adding imaginary number components of the corrected complex baseband signals obtained with respect to said plurality of ultrasonic transducers by said second computing units to one another to generate a phase-matched and added imaginary number signal.

2. The ultrasonic diagnostic apparatus according to claim 1, further comprising:

an image signal generating unit for generating an image signal representing an ultrasonic diagnostic image based on a square root of a sum of squares of the phase-matched and added real number signal and the phase-matched and added imaginary number signal obtained by said adding unit.

3. The ultrasonic diagnostic apparatus according to claim 1, wherein each of said signal processing units includes:

a preamplifier for amplifying the reception signal outputted from respective one of said plurality of ultrasonic transducers;

a low-pass filter for limiting a frequency band of the reception signal outputted from said preamplifier;

an analog/digital converter for converting an analog reception signal outputted from said low-pass filter into a digital reception signal; and an quadrature detection processing unit for performing quadrature detection processing on the digital reception signal converted by said analog/digital converter to generate the complex baseband signal.

4. The ultrasonic diagnostic apparatus according to claim 1, wherein each of said signal processing units includes:

a preamplifier for amplifying the reception signal outputted from respective one of said plurality of ultrasonic transducers;

a first low-pass filter for limiting a frequency band of the reception signal outputted from said preamplifier;

an analog/digital converter for converting an analog reception signal outputted from said first low-pass filter into a digital reception signal;

an quadrature sampling unit for performing quadrature sampling processing on the digital reception signal converted by said analog/digital converter to generate a first signal sequence and a second signal sequence; and second low-pass filters for respectively limiting frequency bands of the first and second signal sequences generated by said quadrature sampling unit to generate the complex baseband signal.

5. The ultrasonic diagnostic apparatus according to claim 1, wherein:

each of said first computing units resamples the amplitude value and the phase value of the complex baseband signal to obtain the amplitude value signal and the phase value signal; and said ultrasonic diagnostic apparatus further comprises at least one memory for storing the amplitude value signal and the phase value signal.

6. A reception focusing processing method comprising the steps of:

(a) generating a complex baseband signal by performing one of quadrature detection processing and quadrature sampling processing on a reception signal outputted from each of a plurality of ultrasonic transducers for transmitting ultrasonic waves according to drive signals and receiving ultrasonic echoes to output reception signals;

(b) obtaining an amplitude value signal representing an amplitude value of the complex baseband signal and a phase value signal representing a phase value of the complex baseband signal generated at step (a), the amplitude value signal and the phase value signal having a predetermined sampling interval;

(c) reading out a phase correction value from a phase correction value table according to a reception direction and correcting the phase value obtained at step (b) by using the phase correction value, said phase correction value table storing phase correction values to be used for correcting the phase value for a time difference according to relative positions of a reception focus and said plurality of ultrasonic transducers, the phase correction values including at least one phase correction value to be used for correcting the phase value for the time difference finer than the predetermined sampling interval;

(d) obtaining a real number component and an imaginary number component of a corrected complex baseband signal represented by the amplitude value obtained at step (b) and the phase value corrected at step (c); and (e) adding real number components of corrected complex baseband signals obtained with respect to said plurality of ultrasonic transducers at step (d) to one another to generate a phase-matched and added real number signal, and adding imaginary number components of the corrected complex baseband signals obtained with respect to said plurality of ultrasonic transducers at step (d) to one another to generate a phase-matched and added imaginary number signal.

7. The reception focusing processing method according to claim 6, further comprising the step of:

(f) generating an image signal representing an ultrasonic diagnostic image based on a square root of a sum of squares of the phase-matched and added real number signal and the phase-matched and added imaginary number signal obtained at step (e).

\* \* \* \* \*